US010626411B2

United States Patent
Liu et al.

(10) Patent No.: US 10,626,411 B2
(45) Date of Patent: Apr. 21, 2020

(54) **GENE FOR ENCODING *BACILLUS THURINGIENSIS* CRYSTAL PROTEINS, AND USE THEREOF**

(71) Applicant: China National Seed Group Corporation, Ltd., Beijing (CN)

(72) Inventors: Bolin Liu, Beijing (CN); Chao Tan, Beijing (CN); Qianqian Yang, Beijing (CN); Jieting Xu, Beijing (CN); Qin Wen, Beijing (CN); Long Qiu, Beijing (CN); Chonglie Ma, Beijing (CN); Wanggen Zhang, Beijing (CN)

(73) Assignee: China National Seed Group Corporation, Ltd., Beijing (CN)

( * ) Notice: Subject to any disclaimer, the term of this patent is extended or adjusted under 35 U.S.C. 154(b) by 20 days.

(21) Appl. No.: 15/746,466

(22) PCT Filed: Jul. 22, 2016

(86) PCT No.: PCT/CN2016/090978
§ 371 (c)(1),
(2) Date: May 16, 2018

(87) PCT Pub. No.: WO2017/012577
PCT Pub. Date: Jan. 26, 2017

(65) Prior Publication Data
US 2018/0362998 A1 Dec. 20, 2018

(30) Foreign Application Priority Data
Jul. 23, 2015 (CN) .......................... 2015 1 0437025

(51) Int. Cl.
*C12N 15/82* (2006.01)
*C12N 15/62* (2006.01)
*C07K 14/325* (2006.01)

(52) U.S. Cl.
CPC ........ *C12N 15/8286* (2013.01); *C07K 14/325* (2013.01); *C12N 15/62* (2013.01)

(58) Field of Classification Search
None
See application file for complete search history.

(56) References Cited

FOREIGN PATENT DOCUMENTS

| CN | 1134981 A | | 11/1996 |
|---|---|---|---|
| CN | 1485430 A | * | 3/2004 |
| CN | 1485430MT | * | 3/2004 |
| CN | 102031266 A | | 4/2011 |
| WO | WO 99/24581 | | 5/1999 |

OTHER PUBLICATIONS

Fang (2013, Genbank Accession #KF303141).*
Sustainable Agriculture Research & Education (SARE) (2012, https://www.sare.org/Learning-Center/Fact-Sheets/Organic-Insect-Management-in-Sweet-Corn/Text-Version/Corn-Earworm).*
Liu et al (2010, Mol. Biol. Rep. 37:677-684).*
Campbell and Gowri, Plant Physiol., 92:1-11 (1990).
Czapla and Lang, J. Econ. Entomol., 83(6):2480-85 (1990).
Dayhoff et al., Atlas of Protein Sequence and Structure (Natl. Biomed. Res. Found., Washington, D.C.) (1978).
International Search Report for International Application No. PCT/CN2016/090978 dated Oct. 28, 2016.
Li et al., ACTA Ecologica Sinica, 32(6):1783-89 (2012) with English Abstract.
Marrone et al., J. Econ. Entomol., 78:290-93 (1985).
Meinkoth and Wahl, Analytical Biochem., 138:267-84 (1984).
Murray et al., Nucleic Acids Res., 17(2):477-98 (1989).
Perlak et al., Bio/Technology, 8:939-43 (1990).
Vaeck et al., Nature, 328:3-37 (1987).
Ye et al., Plant Biotechnology, 18(2):125-33 (2001).
Li and Liu, Chin J Biotech, 31(1):53-64 (2015) with English Abstract.
Frederick et al., Bio/Technology, 8(10):939-43 (1990).

* cited by examiner

*Primary Examiner* — Anne Kubelik
(74) *Attorney, Agent, or Firm* — RatnerPrestia

(57) ABSTRACT

The present disclosure relates to a gene sequence Cry1Ab/Cry1AcZM, an expression cassette containing the gene, an expression vector, a host cell and the use thereof in plant breeding. The protein encoded by an insect-resistant gene according to the disclosure can be expressed in a monocotyledonous plant and further used for culturing an insect-resistant transgenic monocotyledonous plant harboring transgenes Cry1Ab/Cry1AcZM. Bioassay tests prove that the modified and synthesized gene sequence Cry1Ab/Cry1AcZM and the expression product of the constructed vector according to the disclosure have a killing effect on lepidopteran pests.

11 Claims, 7 Drawing Sheets

Specification includes a Sequence Listing.

SEQUENCE LISTING

<160> NUMBER OF SEQ ID NOS: 5

<210> SEQ ID NO 1
<211> LENGTH: 1824
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---:|
| atggattgcc | ggccctacaa | ctgcctgtcg | aaccctgagg | tggaggtcct | gggcggcgag | 60 |
| cggattgaga | ctggctacac | accgattgac | atctcactct | ccctgaccca | gttcctcctg | 120 |
| tcggagttcg | tgccaggcgc | tgggttcgtt | ctcggcctgg | tggatatcat | ttggggcatc | 180 |
| ttcgggccaa | gccagtggga | cgctttcctg | gtccagatcg | agcagctcat | taatcagagg | 240 |
| atcgaggagt | tcgcgcggaa | ccaggctatt | agccgcctcg | agggcctgtc | gaacctctac | 300 |
| cagatctacg | ccgagagctt | cagggagtgg | gaggctgatc | cgacgaaccc | cgccctgagg | 360 |
| gaggagatgc | ggattcagtt | caatgacatg | aactccgctc | tgaccacggc | tatcccactc | 420 |
| ttcgcggtgc | agaattacca | ggtcccactc | ctgagcgtct | acgtgcaggc | tgcgaacctc | 480 |
| cacctgtctg | tgctgcgcga | tgtttcagtg | ttcggccaga | cctgggggtt | cgacgctgct | 540 |
| acgattaatt | ccaggtacaa | cgatctgaca | cggctcatcg | gcaattacac | tgaccatgcc | 600 |
| gttcggtggt | acaacaccgg | cctcgagagg | gtgtgggggc | cagactccag | ggattggatt | 660 |
| aggtacaacc | agttccgcag | ggagctcaca | ctgactgtcc | tggacatcgt | ttccctcttc | 720 |
| ccaaactacg | atagccggac | ctaccctatt | cgcacggtgt | cccagctgac | aagggagatc | 780 |
| tacactaatc | cagtcctcga | gaacttcgac | ggctctttcc | gcgggtcagc | tcagggcatt | 840 |
| gaggggtcca | tcaggagccc | tcacctgatg | gatatcctca | actcaatcac | catctacacg | 900 |
| gacgctcacc | gcggcgagta | ctactggtcc | gggcatcaga | tcatggcttc | cccagtcggc | 960 |
| ttcagcgggc | cagagttcac | cttcccactg | tacggcacga | tggggaacgc | tgctccacag | 1020 |
| cagaggatcg | ttgctcagct | cggccagggg | gtgtaccgca | cactgtccag | cactctctac | 1080 |
| cggcgcccgt | tcaacatcgg | cattaacaat | cagcagctga | gcgtgctcga | cggcacagag | 1140 |
| ttcgcctacg | gacttcgtc | taacctgccc | tcggcggtct | acaggaagtc | gggcaccgtt | 1200 |
| gactctctcg | atgagatccc | gccccagaac | aataacgtcc | cacctcgcca | gggcttctcg | 1260 |
| cacaggctgt | cgcatgtttc | tatgttccgg | tcaggcttct | ccaactcatc | cgtctccatc | 1320 |
| attagggccc | cgatgttctc | atggatccac | cggtccgcgg | agttcaataa | catcattgct | 1380 |
| agcgattcga | tcacgcagat | tccagcggtc | aagggcaatt | tcctcttcaa | cgggagcgtt | 1440 |
| atctcgggcc | ctgggttcac | aggcggggac | ctggtgaggc | tcaatagctc | gggcaataac | 1500 |
| atccagaaca | ggcggtacat | tgaggtccca | atccacttcc | cttctacctc | aacgcgctac | 1560 |
| agggtccggg | ttcgctacgc | gtccgtgaca | ccaattcatc | tgaatgtcaa | ctggggcaat | 1620 |
| tcttcaatct | tctcgaacac | tgtgcctgcc | acagcgactt | ctctggacaa | tctccagtcc | 1680 |
| agcgatttcg | gctacttcga | gtctgctaac | gccttcacct | cgtctctcgg | caatatcgtg | 1740 |
| ggggtccgca | acttcagcgg | cacggctggc | gttattattg | ataggttcga | gttcatccct | 1800 |
| gttactgcta | ccctggaggc | tgag | | | | 1824 |

<210> SEQ ID NO 2
<211> LENGTH: 70
<212> TYPE: DNA
<213> ORGANISM: Artificial Sequence -continued

```
<220> FEATURE:
<223> OTHER INFORMATION: 67-bp Omega sequence and 3-bp Kozak sequence

<400> SEQUENCE: 2
tatttttaca acaattacca acaacaacaa acaacaaaca acattacaat tactatttac      60
aattacaacc                                                             70

<210> SEQ ID NO 3
<211> LENGTH: 148
<212> TYPE: DNA
<213> ORGANISM: Artificial Sequence
<220> FEATURE:
<223> OTHER INFORMATION: Poly A sequence

<400> SEQUENCE: 3
taagtaggtg agtttgagta ttatggcatt ggaaaagcca ttgttctgct tgtaatttac      60
tgtgttcttt cagttttgt tttcggacat caaaaaaaaa aaaaaaaaaa aaaaaaatt       120 taacaaaaaa aaaaaaaaaa aaaaaaaa                                        148

<210> SEQ ID NO 4
<211> LENGTH: 21
<212> TYPE: DNA
<213> ORGANISM: Artificial Sequence
<220> FEATURE:
<223> OTHER INFORMATION: forward primer CSP759

<400> SEQUENCE: 4
cacgcagatt ccagcggtca a                                                21

<210> SEQ ID NO 5
<211> LENGTH: 21
<212> TYPE: DNA
<213> ORGANISM: Artificial Sequence
<220> FEATURE:
<223> OTHER INFORMATION: reverse primer CSP760

<400> SEQUENCE: 5
gacgaggtga aggcgttagc a                                                21
```

GENE FOR ENCODING *BACILLUS THURINGIENSIS* CRYSTAL PROTEINS, AND USE THEREOF

CROSS-REFERENCE TO RELATED APPLICATIONS

This application is a U.S. national phase application of International Application No. PCT/CN2016/090978, filed Jul. 22, 2016, which claims the priority under Article 8 of the PCT to Chinese Patent Application No. 201510437025.2, filed on Jul. 23, 2015, the contents of each of which are incorporated herein by reference in their entireties for all purposes.

FIELD OF THE INVENTION

The disclosure relates to the field of plant biotechnology, and in particular to a Bt insect-resistant gene and the use of its expression vector.

BACKGROUND OF THE INVENTION

Insect pests are a major factor causing the loss of yield of the agricultural crops, and reducing the loss caused by insect pests is an important way to increase the yield and quality of food and feed crops. According to statistics, the loss caused by insect pest attacks on the total yield of food and feed crops in the world has been up to 14% every year, and has directly caused economic losses as high as hundreds of billions of US dollars to agricultural production. Use of the control measures, such as spraying chemical pesticides and biological insecticides, may do reduce the damage of pests to agricultural crops, but chemical pesticides cause environmental pollution, and biological insecticides are expensive. For a long time, spraying large amounts of chemical pesticides will not only enhance pests' resistance to pesticides, and damage beneficial insects and other ecosystems, but also seriously pollute the environments, increase the production costs, and destroy the ecological balance. Therefore, reducing the usage amount of insecticides and developing modern biotechnology has become a problem that must be faced in sustainable development of agriculture.

Maize is an important feed and industrial crop. At present, maize pests mainly include corn borers, which cause serious attacking and significant reduction of maize yield. Therefore, taking effective measures to control the damage thereof is of important significance to improving the maize yield and increasing the rural income. Damage caused by corn borers is one of the important biohazards resulting in reduction of maize yield throughout the year, and seriously affects the output and quality of maize. The corn borers include *Ostrinia furnacalis* and *Ostrinia nubilalis*. China is a district where maize is frequently and seriously attacked by *Ostrinia furnacalis*, and such an attack on a large scale occurs almost once every two years. The yield of maize is reduced by 10% to 15% by corn borers attack in the years of general situation, and may be reduced by as high as 30% or more or even total crop failure in the years under large-scale attack. Due to the damage caused by the corn borers, the loss of maize yield reaches 6-9 million tons every year. The corn borers not only directly cause the loss of maize yield, but also may induce and aggravate the occurrence of maize ear rot, thereby reducing the quality of maize.

At present, the corn borers are still controlled mainly by insecticides and pesticides. An insect-resistant Bt gene may be introduced into maize species using transgenic technology, thus improving the insect resistance of transgenic maize, reducing the usage amount of pesticides, and saving labors, material resources and social resources.

A Bt gene-encoded insecticidal crystal protein from *Bacillus thuringiensis* (Bt for short) is a Gram-positive soil bacillus. In the process of sporulation, Bt produces an insecticidal parasporal crystal protein known as δ-endotoxin. The protein has a very high insecticidal activity. The action principle thereof is that this insect-resistant protein can be dissolved by an alkaline intestinal juice and hydrolyzed to smaller active toxin fragments—the core fragments (Hofte and Whiteley, 1989). Further hydrolysis of the core fragments by protease can be avoided, and the activated proteins bond with the brush vesicles on the intestinal tracts of insects, resulting in perforation and further affecting osmotic balance. Cells expand and then are dissolved. Target organisms stop ingestion and finally die. Researches have shown that the intestinal epithelial cells of many Bt protein-targeted pests have highly affinitive binding sites (Hofte and Whiteley, 1989). Over the past few decades, dozens of *Bacillus thuringiensis* and more than 130 insecticidal crystal proteins encoded by them have been identified. Researches have proven that the Bt crystal protein is nonhazardous for human bodies, mammals, birds, fishes and a lot of beneficial insects, and does not pollute the environment. Therefore, Bt preparations have been applied in agriculture, forestry and environmental health as a nonhazardous natural microbial pesticide for nearly 50 years.

The Bt crystal protein must be ingested by insects to exert the function of killing the insects. However, the Bt crystal protein has poor stability in the natural environment; its insecticidal effect is greatly affected by the weather; it is readily degraded after exposure to sunlight; it cannot penetrate into plant tissues; and it is easily washed away by rain and dew. These factors greatly limit its development and application.

Vaeck et al. (*Nature* 328: 3-37, 1987) obtained a transgenic Bt insect-resistant tobacco having an insecticidal protein for the first time, from which weak insect resistance could be detected, and the expressed protein thereof was almost undetectable, only accounting for 0.001% of the soluble protein. Willbur et al. (*Plant Physiol.* 92: 1-11, 1990) demonstrated through researches that there was a significant difference in the use of codons between low grade biological bacteria and high-grade plants. In addition, there has been evidence that the mRNA transcribed from unstable ATTTA, AATAA or other sequences of tRNA in plants is not complete, so that the translated protein is too short to have an insecticidal activity.

SUMMARY OF THE INVENTION

The disclosure provides an insect-resistant gene Cry1Ab/Cry1AcZM that can be expressed in plants and produce an insect resistance, as well as vectors and host cells containing it. The disclosure further provides the uses of the insect-resistant gene, the expression vectors and the host cells in the insect resistance of transgenic plants.

In one aspect, the disclosure provides an isolated nucleic acid molecule, which comprises a nucleotide sequence as set forth in SEQ ID NO: 1 or a complementary sequence thereof. In an embodiment, the disclosure provides a sequence having at least 90%, at least 95%, at least 98% or at least 99% sequence identity to the gene.

In another aspect, the disclosure provides an expression cassette, which comprises the nucleic acid molecule. In an embodiment, said nucleic acid molecule is operably linked to a Ubi promoter and an Ocs terminator, or to a Ubi promoter and a Nos terminator, or to a CaMV35S promoter and an Ocs terminator, or to a CaMV35S promoter and a Nos terminator.

In a further aspect, the disclosure provides an expression vector, which comprises the expression cassette. In an embodiment, said expression vector further comprises an Ω sequence. In an embodiment, said expression vector further comprises a Kozak sequence. In an embodiment, said expression vector further comprises a PolyA sequence. In an embodiment, said expression vector further comprises a Bar gene.

In another further aspect, the disclosure provides of a host cell, which comprises the expression vector. In an embodiment, said host cell is a plant cell or a prokaryotic cell. In an embodiment, said host cell is an *Escherichia coli* cell or an agrobacterium cell.

In another further aspect, the disclosure provides a method for producing a transgenic plant, wherein the transgenic plant is obtained by transforming a plant by using the expression vector or the host cell. In an embodiment, said plant is a monocotyledonous plant. In an embodiment, said plant is selected from the group consisting of maize, rice, wheat, oat, barley, highland barley, millet, sorghum and sugarcane.

In another further aspect, the disclosure provides a method for producing a transgenic seed, wherein the transgenic seed is produced from the transgenic plant produced by the method for producing the same.

In a further aspect, the disclosure provides a method for controlling the population of a lepidopteran pest, comprising feeding the population of the lepidopteran pest with the transgenic plant obtained by the method disclosed herein. In an embodiment, said plant is a monocotyledonous plant. In an embodiment, said plant is selected from the group consisting of maize, rice, wheat, oat, barley, millet, sorghum and sugarcane. In an embodiment, said lepidopteran pest is *Ostrinia furnacalis* or *Ostrinia nubilalis*.

In another further aspect, the disclosure provides a method for killing a lepidopteran pest, comprising feeding the lepidopteran pest with an insecticidally effective amount of the transgenic plant obtained by the method disclosed herein. In an embodiment, said plant is a monocotyledonous plant. In an embodiment, said plant is selected from the group consisting of maize, rice, wheat, oat, barley, millet, sorghum and sugarcane. In an embodiment, said lepidopteran pest is *Ostrinia furnacalis* or *Ostrinia nubilalis*.

In a further aspect, the disclosure provides a method for reducing the damage of a lepidopteran pest to a plant comprising stably integrating an expression vector into the genome of the plant, wherein said expression vector comprises a nucleic acid molecule encoding a lepidopteran pest-resistant gene, and said nucleic acid molecule comprises a nucleotide sequence as set forth in SEQ ID NO: 1 or a nucleotide sequence having at least 90%, at least 95%, at least 98% or at least 99% sequence identity to SEQ ID NO: 1, or a complementary sequence thereof. In an embodiment, said plant is a monocotyledonous plant. In an embodiment, said plant is selected from the group consisting of maize, rice, wheat, oat, barley, millet, sorghum and sugarcane. In an embodiment, said lepidopteran pest is *Ostrinia furnacalis* or *Ostrinia nubilalis*.

In another further aspect, the disclosure provides a transgenic plant comprising an expression cassette integrated into a genome thereof, wherein said expression cassette comprises a nucleic acid molecule encoding a lepidopteran pest-resistant gene, said nucleic acid molecule comprises the nucleotide sequence as set forth in SEQ ID NO: 1 or a nucleotide sequence having at least 90%, at least 95%, at least 98% or at least 99% sequence identity to SEQ ID NO: 1, or a complementary sequence thereof. In an embodiment, the disclosure provides a nucleic acid sequence having at least 90%, at least 95%, at least 98% or at least 99% sequence identity to the gene. In some embodiments, said nucleic acid molecule comprises the nucleotide sequence as set forth in SEQ ID NO: 1 or the nucleic acid molecule consists of the nucleotide sequence as set forth in SEQ ID NO: 1. In some embodiments, said plant is a monocotyledonous plant. In some embodiments, said plant is selected from the group consisting of maize, rice, wheat, oat, barley, millet, sorghum and sugarcane. In some embodiments, the disclosure further relates to organs, tissues and cells of the plant, as well as processed products, such as food and feed, produced from said plant.

In some embodiments, the insect-resistant gene Cry1Ab/Cry1AcZM disclosed herein can be stably and efficiently expressed in plants, and has a good insecticidal effect.

BRIEF DESCRIPTION OF THE DRAWINGS

FIG. 1A-K are schematic diagrams of intermediate vectors and transformation vectors, where FIG. 1A shows vector pZZ01205; FIG. 1B shows vector pZZ0015; FIG. 1C shows transformation vector pZHZH25017; FIG. 1D shows vector pZZ01206; FIG. 1E shows transformation vector pZHZH25018; FIG. 1F shows vector pZZ01207; FIG. 1G shows vector pZZ00005; FIG. 1H shows transformation vector pZHZH25020; FIG. 1J shows vector pZZ01228; and FIG. 1K shows transformation vector pZHZH25022. Meanings of the vector map in English and abbreviations thereof in FIG. 1A to FIG. 1K are listed below:

Ubi promoter: Ubiquitin promoter
Omega: Omega sequence
Cry1Ab/Cry1AcZM: Optimized Bt gene sequence
polyA: Polyadenylic acid sequence
T-NOS: Nopaline synthetase terminator
T-OCS: Octopine synthetase terminator
pMB1 rep: pMB1 replicon
Amp(R): Amicillin resistance
EGFP: Green fluorescent protein
T-Border (right): T-DNA right border sequence
CaMV35S promoter: Cucumber mosaic virus 35S promoter
BAR: glufosinate-resistant gene sequence
CaMV35S polyA: Polyadenylic acid sequence of cucumber mosaic virus 35S
T-Border(left): T-DNA left border sequence
Bp: Base pair
Kanamycin (R): Kanamycin-resistant sequence
pBR322 ori: pBR322 originator sequence
pBR322 born: pBR322 backbone sequence
pVS1 rep: pVS1 replicon
pVS1 sta: pVS1 transcription start region

Figure 4:
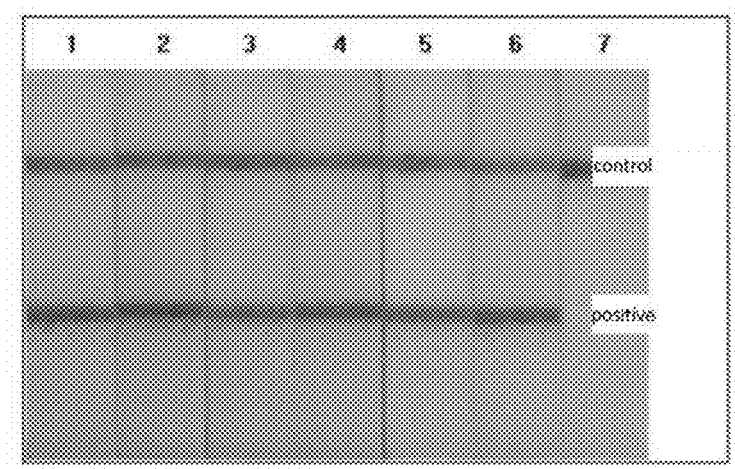

FIG. 4 is a diagram of the result of identifying a T0 generation plant using an immunostrip, where numbers 1-2 are samples of a plant (transformation vector pZHZH25017); numbers 3-4 are samples of a plant (transformation vector pZHZH25018); number 5 is a sample of a plant (transformation vector pZHZH25020); number 6 is a positive sample of a plant (transformation vector pZHZH25022), and number 7 is a negative control sample.

Figure 2:
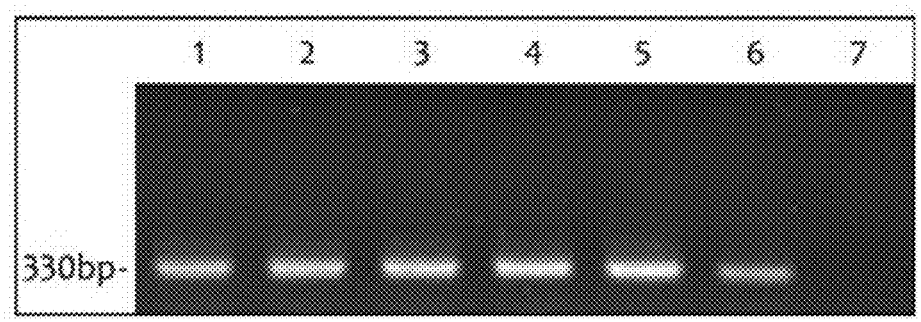
FIG. 2 shows the results of identifying a T0 generation plant by PCR, where lanes 1-6 are different T0 generation transgenic plants, being positive, while lane 7 is negative control, and the molecular weight of the positive band is 333 bp.
Figure 3:
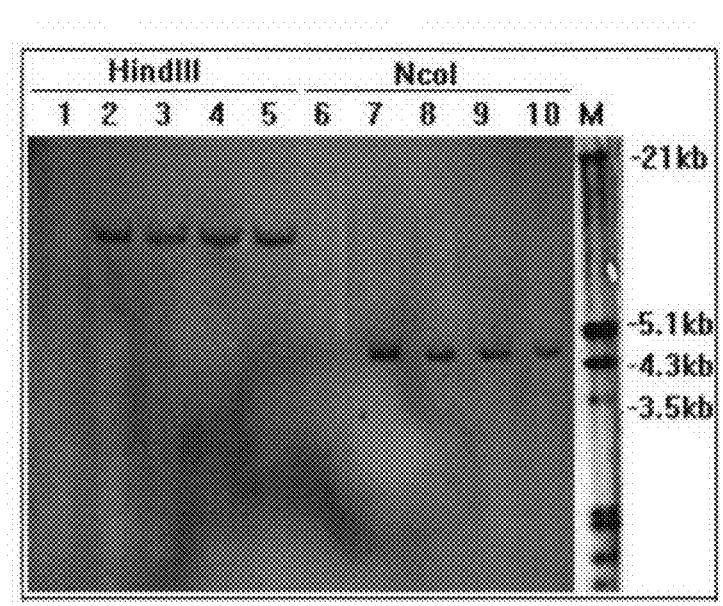
FIG. 3 is a diagram of the Southern blot test result of genomic DNA in a transformed maize plant, i.e., the result of molecular hybridization of HindIII-digested and NcoI-digested genomic DNA of a T1 generation maize plant transformed by a vector pZHZH25017 respectively to a Cry1Ab/Cry1AcZM-specific probe having a length of 333 bp. Lanes 1 and 6 are for negative control Xiang 249; lanes 2 and 7 are for T1-1; Lanes 3 and 8 are for T1-2; Lanes 4 and 9 are for T1-3; and lanes 5 and 10 are for T1-4 material. Under either of the enzyme digestion conditions, a positive band is respectively observed, indicating that a single copy of an exogenous gene is inserted. M is for lane with a molecular weight marker with the number of base pairs marked.
Figure 5A:
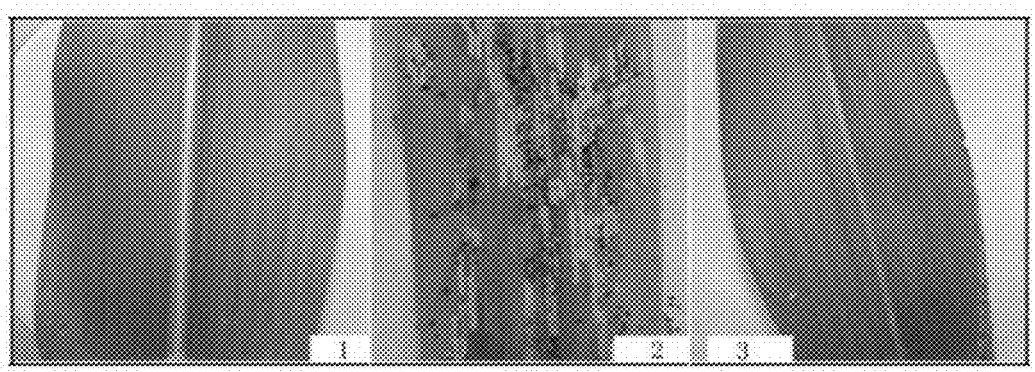
Figure 5B:
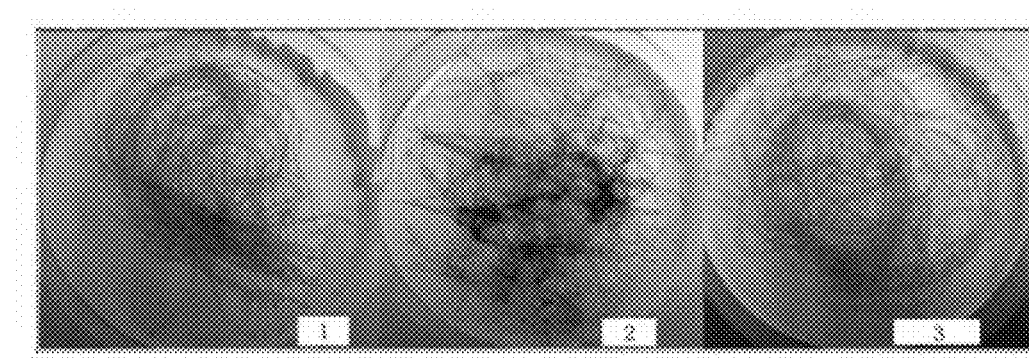

FIG. 5A is a diagram of the insect resistance bioassay result of detached leaves on T0 generation maize, where FIG. 5A-1 is an insect-resistant leaf (transformation vector pZHZH25018); FIG. 5A-2 is a negative control Xiang 249; and FIG. 5A-3 is a positive control sample (Cry11Ac). FIG. 5B is a diagram of the insect resistance bioassay result of detached filaments on T0 generation maize, where FIG. 5B-1 is an insect-resistant filament (transformation vector pZHZH25018); FIG. 5B-2 is a negative control Xiang 249; and FIG. 5B-3 is a positive control sample (Cry11Ac).

DETAILED DESCRIPTION OF THE INVENTION

Unless otherwise indicated, nucleic acids are written from left to right in the 5' to 3' direction; amino acid sequences are written from left to right in the direction from amino to carboxyl terminals. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Numeric ranges are inclusive of the numbers defining the range.

As used herein, the term "nucleic acid" includes reference to polymers of deoxyribonucleotide or ribonucleotide in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein, the term "encoding" or "encoded" when used in the context of a specified nucleic acid means that the nucleic acid comprises the requisite information to direct translation of the nucleotide sequence into a specified protein. The information by which a protein is encoded is specified by the use of codons. As used herein, the term "full-length sequence" refers to a specified polynucleotide or its encoded protein means having the entire nucleic acid sequence or the entire amino acid sequence of a native (non-synthetic) endogenous sequence. A full-length polynucleotide encodes the full-length, catalytically active form of the specified protein.

The terms "polypeptide", "peptide" and "protein" are used interchangeably herein to refer to a polymer of amino acid residues. The terms apply to amino acid polymers in which one or more amino acid residues are artificial chemical analogues of corresponding naturally occurring amino acids, as well as to naturally occurring amino acid polymers.

The terms "residue", "amino acid residue" and "amino acid" are used interchangeably herein to refer to an amino acid that is incorporated into a protein, polypeptide or peptide (collectively known as "protein"). The amino acid may be a naturally occurring amino acid and, unless otherwise limited, may encompass known analogs of natural amino acids that can function in a similar manner as naturally occurring amino acids.

The terms "isolated" and "purified" are used interchangeably herein to refer to a nucleic acid or a polypeptide or a biologically active moiety thereof, which is substantially or essentially free of components normally accompanying or interacting with the nucleic acid or the polypeptide as found in its naturally occurring environment. Thus, an isolated or purified nucleic acid or polypeptide is substantially free of other cellular materials or culture media when produced by recombinant techniques, or substantially free of chemical precursors or other chemicals when chemically synthesized.

An "isolated" nucleic acid is usually free of sequences (such as, for example, protein encoding sequences) that naturally flank the nucleic acid (i.e., sequences located at the 5' and 3' ends of the nucleic acid) in the genomic DNA of the organism from which the nucleic acid is derived. In various embodiments, the isolated nucleic acid can contain nucleotide sequences, for example less than about 0.5 KB, naturally flanking the nucleic acid in the genomic DNA of the cell from which the nucleic acid is derived.

Throughout the disclosure, the word "comprising", "comprises" or variations thereof will be understood to imply the inclusion of a stated element, integer or step, or group of elements, integers or steps, but not the exclusion of any other element, integer or step, or group of elements, integers or steps.

As used herein, the term "impacting insect pests" refers to affecting changes in insect feeding, growth, and/or behavior at any stage of development, including but not limited to: killing the insect, retarding growth, preventing reproductive capability, antifeedant activity, and the like.

As used herein, the term "insecticidal activity" refers to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having insecticidal activity adversely impacts at least one measurable parameter of pest fitness. For example, "insecticidal proteins" are proteins that display insecticidal activity by themselves or in combination with other proteins.

As used herein, the term "pesticidally effective amount" refers to a quantity of a substance or organism that has pesticidal activity when present in the environment of a pest. Similarly, an "insecticidally effective amount" may be used to refer to a "pesticidally effective amount" when the pest is an insect pest.

As shall be understood, the term "transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

A "subject plant" or "subject plant cell" is one in which genetic alteration has been effected, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

A person skilled in the art will readily acknowledge that advances in the field of molecular biology such as site-specific and random mutagenesis, polymerase chain reaction methodologies, and protein engineering techniques provide an extensive collection of tools and operating steps suitable for use to alter or engineer both the amino acid sequence and potential genetic sequences of proteins of agricultural interest.

In some embodiments, the nucleotide sequences of the disclosure may be altered for conservative amino acid substitutions. The principles and examples for such conservative amino acid substitutions will be further described hereinafter. In some embodiments, nucleotide sequences of the present disclosure may be substituted without changing the amino acid sequences based on codon preferences of monocotyledonous plants as disclosed in FIG. 1. For example, codons encoding a given amino acid sequence may be substituted with codons preferred by a monocotyledonous plant, but the amino acid sequence encoded by the nucleotide sequence is not changed.

The disclosure further relates to nucleotide sequences obtained by further optimization of SEQ ID NO: 1. More details of the method are described by Murray et al. (1989) *Nucleic Acids Res.* 17:477-498. The optimized nucleotide sequences may be used to improve the expression of insecticidal proteins in plants, which may be, for example, monocotyledonous plants, for example, graminaceous plants, for example, *Zea mays*. As used herein, the term "mutated nucleotide sequence" or "mutation" or "mutagenized nucleotide sequence" connotes a nucleotide sequence that has been mutagenized or altered to contain one or more nucleotide residues (e.g., base pair) that are not present in the corresponding wild-type sequence.

In some embodiments, parts of the nucleotide sequences in the disclosure are substituted with different codons encoding a given amino acid sequence, thus changing the nucleotide sequence without changing its encoded amino acid sequence. Conservative variants include those sequences that, because of the degeneracy of the genetic codons, encode the amino acid sequence of one of the insecticidal polypeptides of the embodiments. In some embodiments, parts of nucleotide sequences in the disclosure are replaced based on codon preferences of monocotyledonous plants.

In some embodiments, mutant nucleotide sequences further include synthetically derived nucleotide sequences, such as those generated, for example, by using site-directed mutagenesis but which still encode a pesticidal protein of the embodiments, such as a mutant toxin. In some embodiments, such mutant nucleotide sequences further include additions, deletions or replacements of one or more nucleic acid residues. In some embodiments, such addition, removal or replacement may lead to addition, removal or replacement of the corresponding amino acid residue. Generally, variants of a particular nucleotide sequence of the embodiments will have at least about 90% or more sequence identity to that particular nucleotide sequence as determined by sequence alignment programs described below. A variant of a nucleotide sequence of the embodiments may differ from the sequence of the disclosure by as few as 1-15 nucleotides, as few as 1-10, such as 6-10, as few as 5, as few as 4, 3, 2, or even 1 nucleotide.

In some embodiments, mutant nucleotide sequence can encode a mutant protein having improved or decreased insecticidal activity. Such pesticidal activity may be different or improved relative to the native protein or it may be unchanged, so long as pesticidal activity is retained. Variant protein encompasses polypeptides that are derived from a native protein. The derivation can be achieved by deletion (so-called truncation) of one or more amino acids at the N-terminal and/or C-terminal end of the native protein; addition of one or more amino acids to the N-terminal and/or C-terminal end of the native protein; deletion or addition of one or more amino acids at or to one or more sites in the native protein; or substitution of one or more amino acids at one or more sites in the native protein.

Variant proteins encompassed by the embodiments are biologically active, that is, they continue to possess the desired biological activity of the native protein, that is, pesticidal activity as described herein. Such variants may result from, for example, genetic polymorphism or human manipulation. It will be appreciated by those skilled in the art that any useful mutation may be added to the sequences of the embodiments so long as the encoded polypeptides retain pesticidal activity. The amino acid sequence of a mutant protein of some embodiments will have at least about 90% or more sequence identity to the amino acid sequence of the protein in the disclosure. A mutant protein of some embodiments may differ from the protein in the disclosure by as few as 1-15 amino acid residues.

In some embodiments, sequences may also be mutated so that the encoded polypeptides are resistant to proteolytic digestion by protease. Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Proteolytic sites and putative proteolytic sites include, but are not limited to, the following sequences: a trypsin cleavage site, a chymotrypsin site and a trypsin site. These sites may be altered by the addition or deletion of any number and kind of amino acid residues, so long as the pesticidal activity of the polypeptide is enhanced. Thus, polypeptides encoded by nucleotide sequences comprising mutations will comprise at least one amino acid change or addition relative to the native or background sequence, or 50 or more amino acid changes or additions.

Those skilled in the art would recognize that amino acid additions and/or substitutions are generally based on the relative similarity of the amino acid side-chain substituents, for example, their hydrophobicity, charge, size, and the like. Exemplary amino acid substituent groups that take various of the foregoing characteristics into consideration are well known to those skilled in the art and include: arginine and lysine; glutamate and aspartate; serine and threonine; glutamine and asparagine; and valine, leucine and isoleucine. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), incorporated herein by reference. Conservative substitutions, such as exchanging one amino acid with another having similar properties, may be made.

When it is difficult to predict the exact effect of the substitution, deletion or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, incorporated herein by reference.

In some embodiments, full-length coding sequences, sequence motifs encoding a structural domain of interest, or any fragment of a nucleotide sequence of the embodiments may be recombined between the nucleotide sequences of the embodiments and corresponding portions of other known Cry nucleotide sequences to obtain a new gene with an improved property.

Properties of interest include, but are not limited to, pesticidal activity per unit of pesticidal protein, protein stability, and toxicity to non-target species particularly humans, livestock, and plants and microbes that express the pesticidal polypeptides of the embodiments. The embodiments are not limited by a particular rearrangement strategy. Rearrangement may involve only nucleotide sequences disclosed herein or may additionally involve rearrangement of other nucleotide sequences known in the art. Strategies for DNA rearrangement are known in the art.

Identification of sequence identity includes a hybridization technique. For example, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides, and may be labeled with a detectable group such as $^{32}P$ or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art.

In some embodiments, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a detecting assay to determine the presence of coding sequences in an organism. Hybridization techniques include hybridization screening of plated DNA libraries.

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

Specificity is typically dependent on post-hybridization washing, with the critical factors being the ionic strength and temperature of the final washing solution. For DNA-DNA hybrids, the $T_m$ (thermal melting point) can be approximated from the equation of Meinkoth and Wahl (1984) *Anal. Biochem.* 138:267-284: $T_m$=81.5° C.+16.6(log M)+0.41 (% GC)−0.61 (% formamide)−500/L; where M is the molarity of monovalent cations, % GC is the percentage of guanosine and cytosine nucleotides in the DNA, "% formamide" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Washing is typically performed at least until equilibrium is reached and a low background level of hybridization is achieved, such as for 2 hours, 1 hour or 30 minutes.

$T_m$ is reduced by about 1° C. for each 1% of mismatching; thus, $T_m$, hybridization and/or washing conditions can be adjusted to hybridize to sequences of the desired identity. For example, if sequences with ≥90% identity are sought, the $T_m$ can decrease by 10° C. Generally, stringent conditions are selected to be about 5° C. lower than the $T_m$ for the specific sequence and its complementary sequence at a defined ionic strength and pH. However, severely stringent conditions can utilize a hybridization and/or wash at 4° C. lower than the $T_m$; moderately stringent conditions can utilize a hybridization and/or washing at 6° C. lower than the $T_m$; low stringency conditions can utilize a hybridization and/or washing at 11° C. lower than the $T_m$.

Fragments of the nucleotide sequences and the amino acid sequences encoded thereby are also encompassed by some embodiments. As used herein, the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. The variant protein encompasses biologically active fragments of a native protein that comprise a sufficient number of contiguous amino acid residues to retain the biological activity of the native protein.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. In some embodiments, pesticidal activity of a polypeptide may also be improved by truncation of the native or full-length sequence.

Thus, in some embodiments, the present disclosure relates to truncated versions or fragments of the full-length insecticidal polypeptides. Some of the polypeptide fragments, variants and mutations of some embodiments will have enhanced pesticidal activity relative to the activity of the naturally occurring insecticidal polypeptide from which they are derived. Some of the polypeptide fragments, variants and mutations of some embodiments will have reduced pesticidal activity relative to the activity of the naturally occurring insecticidal polypeptide from which they are derived.

A fragment of a nucleotide sequence of the embodiments that encodes a biologically active portion of a pesticidal protein of the embodiments will encode at least 50 contiguous amino acids, or up to the total number of amino acids present in a pesticidal polypeptide of the embodiments. Nucleic acids that are fragments of a nucleotide sequence of the embodiments comprise at least 150 nucleotides, or up to the number of nucleotides present in a nucleotide sequence disclosed herein. Particular embodiments envision fragments derived from (e.g., produced from) a first nucleic acid of the embodiments, wherein the fragment encodes a truncated toxin characterized by pesticidal activity. Truncated polypeptides encoded by the polynucleotide fragments of the embodiments are characterized by pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' ends of the native or corresponding full-length coding sequence.

The disclosure relates to an expression cassette comprising the isolated nucleic acid molecule. The disclosure does not limit the promoter and terminator specifically used in the expression cassette, as long as they are applicable for expression in plants. In some embodiments, the nucleic acid molecule is operably linked to a 35S promoter and a Nos terminator.

The disclosure further relates to an expression vector comprising the isolated nucleic acid molecule. In some embodiments, the expression vector comprises the expression cassette. In some embodiments, the expression vector further comprises a PolyA sequence and an omega enhancer.

In some embodiments, the expression vector further comprises other expression cassettes for detecting the expression of the expression vector in cells.

Some embodiments further encompass a microorganism, such as *Escherichia coli* or agrobacterium, that is transformed with at least one nucleic acid of the embodiments, with an expression cassette comprising the nucleic acid, or with a vector comprising the expression cassette. In some embodiments, the microorganism is the one that multiplies relying on the plants.

Some embodiments further comprise transformed plant cells or transgenic plants comprising at least one nucleotide sequence of the embodiments. In some embodiments, a plant is transformed using an expression vector comprising at least one nucleotide sequence of the embodiments and a promoter that is operably linked thereto and drives expression in a plant cell. The transformed plant cell and transgenic plant refer to a plant cell or plant that comprises within its genome a heterologous polynucleotide. Generally, the heterologous polynucleotide is stably integrated within the genome of a transformed plant cell or transgenic plant such that the polynucleotide is passed on to successive generations. The heterologous polynucleotide may be integrated into the genome alone or as part of an expression vector.

In some embodiments, the plant as referred to in the disclosure is a monocotyledonous plant; and optionally, the plant is selected from the group consisting of maize, rice, wheat, oat, barley, highland barley, millet, sorghum and sugarcane.

In some embodiments, the plant as referred to in the disclosure includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The disclosure further includes plant cells, protoplasts, tissues, callus, embryos as well as flowers, stems, fruits, leaves, and roots originating in transgenic plants or progeny thereof of the disclosure, and therefore consisting at least in part of the nucleotide sequences as disclosed herein.

Although the embodiments do not depend on a particular biological mechanism for increasing the resistance of a plant to a plant pest, expression of the nucleotide sequences of the embodiments in a plant can result in the production of the pesticidal proteins of the embodiments and in an increase in the resistance of the plant to a plant pest. The plants of the embodiments find use in agriculture in methods for impacting insect pests. Certain embodiments provide a transformed agricultural crop plant, which finds use in methods for impacting insect pests of the plant, such as, for example, a lepidopteran pest.

The Lepidopteran pests include, but are not limited to, the pests in the family Noctuidae: *Spodoptera frugiperda, Spodoptera exigua, Spodoptera litura, Mamestra configurata, Mamestra brassicae, Agrotis ipsilon, Agrotis orthogonia, Agrotis segetum, Alabama argillacea, Trichoplusia ni, Pseudoplusia* includes, *Anticarsia gemmatalis, Hypena scabra, Heliothis virescens, Pseudaletia unipuncta, Athetis mindara, Euxoa messoria, Earias insulana, Earias vittella, Helicoverpa armigera, Helicoverpa zea*; pests in the family Pyralidae: *Ostrinia furnacalis, Ostrinia nubilalis, Amyelois transitella, Anagasta kuehniella, Cadra cautella, Chilo suppressalis, Chilo partellus, Corcyra cephalonica, Crambus caliginosellus, Crambus teterrellus, Cnaphalocrocis medinalis, Desmia funeralis, Diaphania hyalinata, Diatraea grandiosella, Diatraea saccharalis, Eoreuma loftini, Ephes-* tia elutella, Galleria mellonella, Herpetogramma licarsisalis, Homoeosoma electellum, Elasmopalpus lignosellus, Achroia grisella, Loxostege sticticalis, Maruca testulalis, Plodia interpunctella, Scirpophaga incertulas and Udea rubigalis; pests in the family Tortricidae: Acleris variana, Archips argyrospila, Archips rosana, Argyrotaenia citrana, Choristoneura rosaceana; and pests in other families: Adoxophyes orana, Cochylis hospes, Cydia latiferreana, Cydia. Pomonella, Platynota flavedana, Platynota stultana, Lobesia botrana, Spilonota ocellana, Endopiza viteana, Eupoecilia ambiguella, Bonagota salubricola, Grapholita molesta, Suleima helianthana, etc.

Other selected agricultural lepidopteran pests include, but are not limited to, Alsophila pometaria, Bucculatrix thurberiella, Colias eurytheme, Datana integerrima, Ennomos subsignaria, Erannis tiliaria, Euproctis chrysorrhoea, Harrisina Americana, Hyphantria cunea, Keiferia lycopersicella, Lambdina fiscellaria, Lambdina fiscellaria lugubrosa, Leucoma salicis, Lymantria dispar, Manduca quinquemaculata, Manduca sexta, Operophtera brumata, Paleacrita vernata, Papilio cresphontes, Phryganidia californica, Phyllocnistis citrella, Phyllonorycter blancardella, Pieris brassicae, Pieris rapae, Pieris napi, Plutella xylostella, Pectinophora gossypiella, Sabulodes aegrotata, Sitotroga cerealella, Thaumetopoea pityocampa, Tineola bisselliella, Tuta absoluta and Yponomeuta padella.

EXAMPLES

Example 1: Design and Synthesis of Insect-Resistant Gene

The gene in the disclosure is based on a 608 amino acid sequence of N-terminal of the fusion protein after fusion and modification of Cry1Ab and Cry1Ac, and the coding sequences were replaced with codons preferred by plants. After eliminating restriction enzyme digestion sites rich in AT sequence and common restriction enzyme digestion sites resulting in unstable transcription of plants present in the DNA sequence, corrections and eliminations were carried out by replacing the codons; a modified DNA sequence was obtained by adding a termination codon TAA at the 3' end; and a modified Bt gene, such as sequence SEQ ID NO: 1 was identified and chemically synthesized. A protein encoded by the modified DNA sequence contains three functional zones, where two functional zones at the N-terminal are highly homologous to the counterpart of Cry1Ab, and the functional zone at the C-terminal is highly homologous to Cry1Ac. Therefore, the gene in the disclosure was named Cry1Ab/Cry1AcZM. A homologous comparison between the sequence, the sequence of Guo Sandui et al. (CN1037913C, 1996) and Cry1Ab in transgenic maize plant Mon810 of Monsanto was carried out (results as shown in Table 1), and the GC content was calculated (results as shown in Table 2).

TABLE 1

Homologous Comparison between DNA Sequences

| Comparison between DNA sequence | Cry1Ab/Cry1AcZM |
|---|---|
| CN1037913C | 74.9% |
| Mon810 | 71.4% |

TABLE 2

GC Content Percentage in Cry1Ab/Cry1AcZM and Affinis Sequences

| Sequence name | GC percentage % |
|---|---|
| Cry1Ab/Cry1AcZM | 58 |
| CN1037913C | 48 |
| Mon810 | 61 |

Example 2: Vector Construction

Based on the needs for expressing gene functions in plants, expression optimization was further designed for the upstream and the downstream of the Cry1Ab/Cry1AcZM gene coding region, in order to improve the strength of the gene in the transcriptional level and the efficiency of the protein translation, including adding a fragment of an omega (Ω) sequence consisting of 67 nucleotides and a Kozak sequence (SEQ ID NO: 2) consisting of 3 nucleotides (acc) to the 5' end to enhance the translational efficiency of eukaryotic genes, and a fragment of poly(A) tail sequence (SEQ ID NO: 3) of eukaryotic mRNA to the 3' end to increase transport from the karyon to the cytoplasm, mRNA stability and translational efficiency.

HindIII and PstI digestion sites were added to the 5' end of the synthesized SEQ ID NO: 1, and PmeI digestion site was added to the 3' end. The synthesized sequence was cloned on a Puc57simple vector, and was named pzz01194.

Figure 1A:
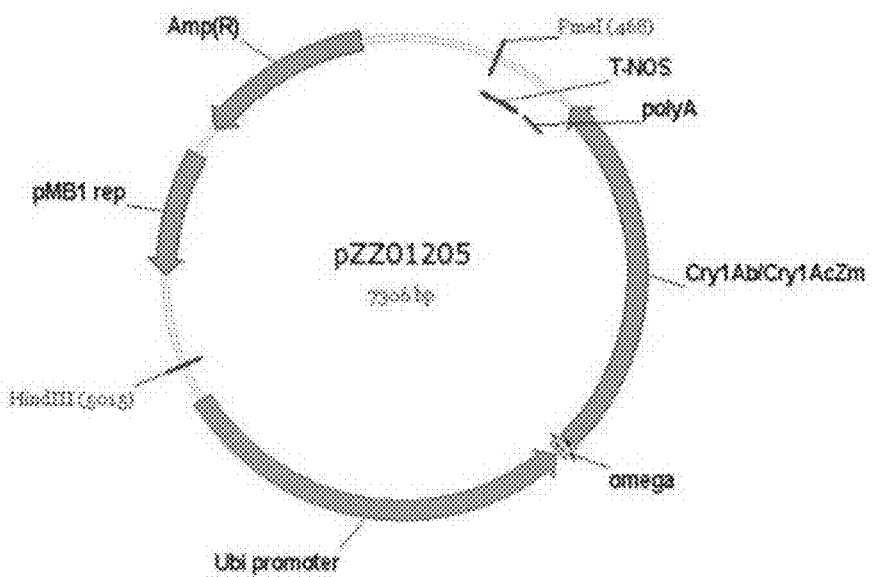

Four plant expression vectors were constructed, and were respectively described as follows:

(I) Construction of pZHZH25017:

pzz00002 was digested with restriction enzymes HindIII and BamHI to obtain a Ubi promoter fragment, and a sticky end produced therefrom was blunted with T4DNA polymerase.

pzz01194 was digested with a restriction enzyme PstI, a sticky end produced therefrom was blunted with T4DNA polymerase, and the Ubi promoter was linked thereto through a blunt end connection type to obtain a vector named pzz01201 containing a fragment Ubi-Cry1Ab/Cry1AcZM.

pzz01188 was singly-digested with an enzyme EcoRI to obtain a Tnos terminator fragment, and a sticky end produced therefrom was blunted with T4DNA polymerase.

pzz01201 was digested with PmeI, and a Tocs terminator was linked thereto through a blunt end connection type to obtain a vector named pzz01205 containing a fragment Ubi-Cry1Ab/Cry1AcZM-Tnos (FIG. 1A).

pzz00002 was digested with HindIII+BamHI to obtain a Ubi promoter fragment, and a sticky end produced therefrom was blunted with T4DNA polymerase.

pzz01194 was digested with PstI, a sticky end produced therefrom was blunted with T4DNA polymerase, and the Ubi promoter was linked thereto through a blunt end connection type to obtain a vector named pzz01201 containing a fragment Ubi-Cry1Ab/Cry1AcZM.

An existing vector containing the Tnos terminator (with EcoRI digestion site at the 5' end, and PmeI and EcoRI sites at the 3' end) was named pzz01188, and the Tnos termination sequence can be obtained by single digestion of pzz01188 with EcoRI.

Figure 1B:
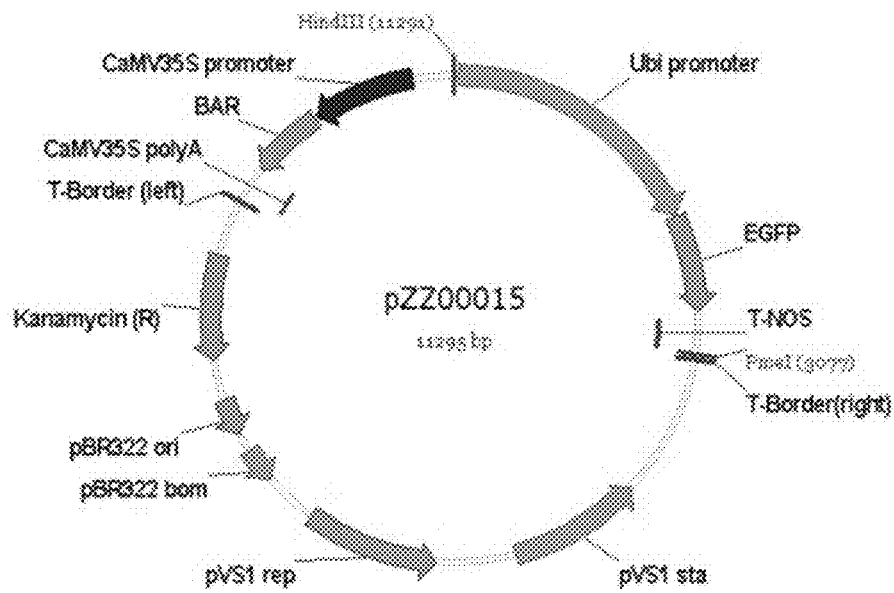

A Tnos terminator fragment was obtained by single digestion of pzz01188 with EcoRI, and a sticky end produced therefrom was blunted with T4DNA polymerase.

pzz01201 was digested with PmeI, and the Tocs terminator was linked thereto through a blunt end connection type to obtain a vector pzz00015 containing a fragment Ubi-Cry1Ab/Cry1AcZM-Tnos (FIG. 1B).

An element Ubi-EGFP-T35spolyA was added to the backbone of the constructed vector pzz00015 (FIG. 1B), i.e., pCambia3300 (with an element 35s-BAR-T35spolyA), by double digestion with HindIII+PmeI, and the element Ubi-EGFP-T35spolyA was removed with HindIII+PmeI; and then a new element was added to the sites.

A vector pzz01205 was digested with HindIII+PmeI to obtain a fragment Ubi-Cry1Ab/Cry1AcZM-Tnos.

Figure 1C:
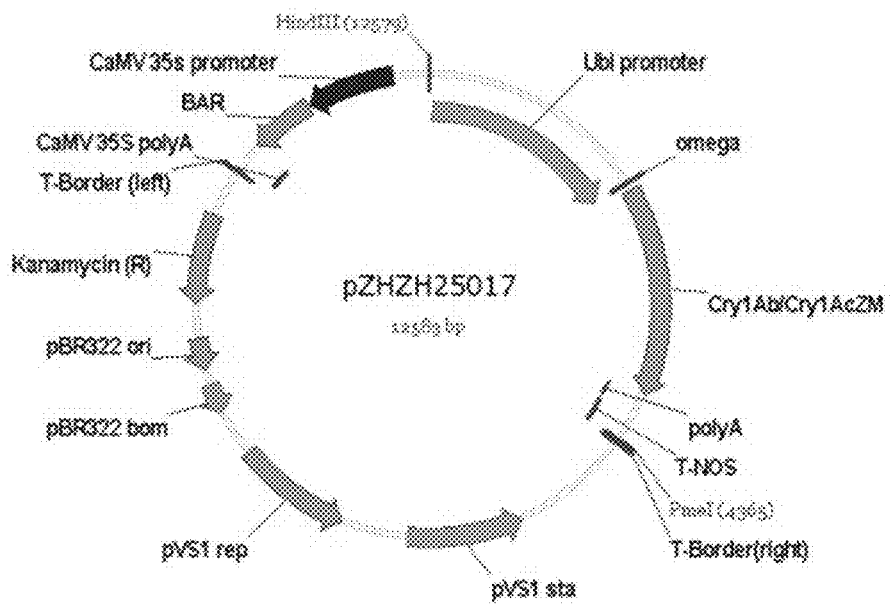

The vector pzz00015 was digested with HindIII+PmeI, and Ubi-Cry1Ab/Cry1AcZM-Tnos was linked to the digestion sites to obtain an expression vector named pZHZH25017 containing two expression elements, i.e., Ubi-Cry1Ab/Cry1AcZM-Tnos and 35s-BAR-T35spolyA, as shown in FIG. 1C.

(II) Construction of pZHZH25018:

pzz01194 was digested with a restriction enzyme PstI, and a sticky end produced therefrom was blunted with T4DNA polymerase, and the Ubi promoter was linked thereto through a blunt end connection type to obtain a vector named pzz01201 containing a fragment Ubi-Cry1 Ab/Cry1AcZM. A vector pzz00002 containing the Ubi promoter was digested with restriction enzymes HindIII+BamHI to obtain a Ubi promoter fragment, and a sticky end produced therefrom was blunted with T4DNA polymerase.

Figure 1D:
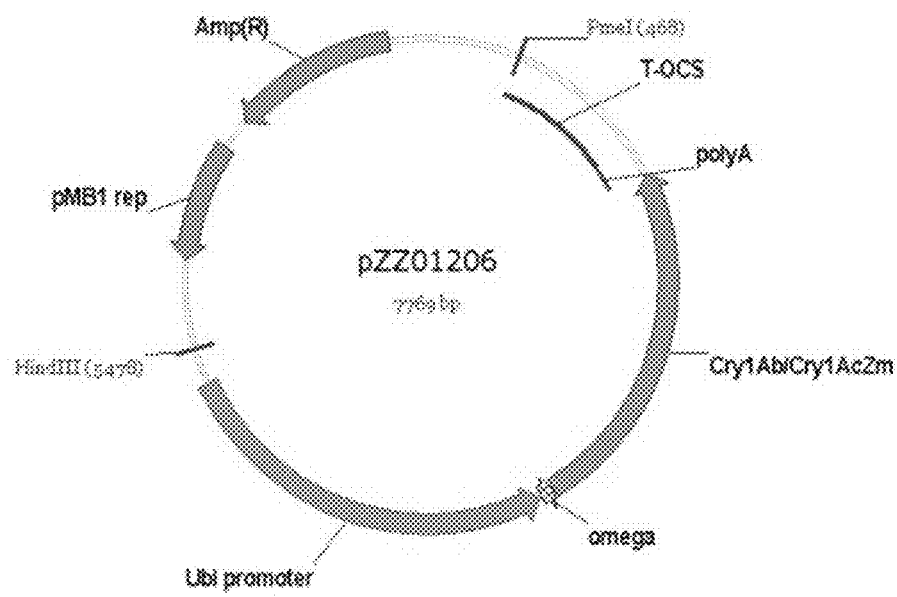

An existing vector containing the Tocs terminator (with EcoRI digestion site at the 5' end, and with PmeI and EcoRI sites at the 3' end) was named pzz01131, and the Tocs termination sequence can be obtained by single digestion of pzz01131 with EcoRI.

pzz01131 was digested with EcoRI to obtain a Tocs terminator fragment, and a sticky end produced therefrom was blunted with T4DNA polymerase.

pzz01201 was digested with PmeI, and the Tocs terminator was linked thereto through a blunt end connection type to obtain a vector named pzz01206 containing a fragment Ubi-Cry1Ab/Cry1AcZM-Tocs (FIG. 1D).

An element Ubi-EGFP-T35spolyA was added to a constructed vector pzz00015 with pCambia3300 (with an element 35s-BAR-T35spolyA) as its backbone by double digestion with HindIII+PmeI, Ubi-EGFP-T35spolyA can be removed with HindIII+PmeI, and then a new element was added to the sites.

The vector pzz01206 was digested with HindIII+PmeI to obtain a fragment Ubi-Cry1Ab/Cry1AcZM-Tocs.

Figure 1E:
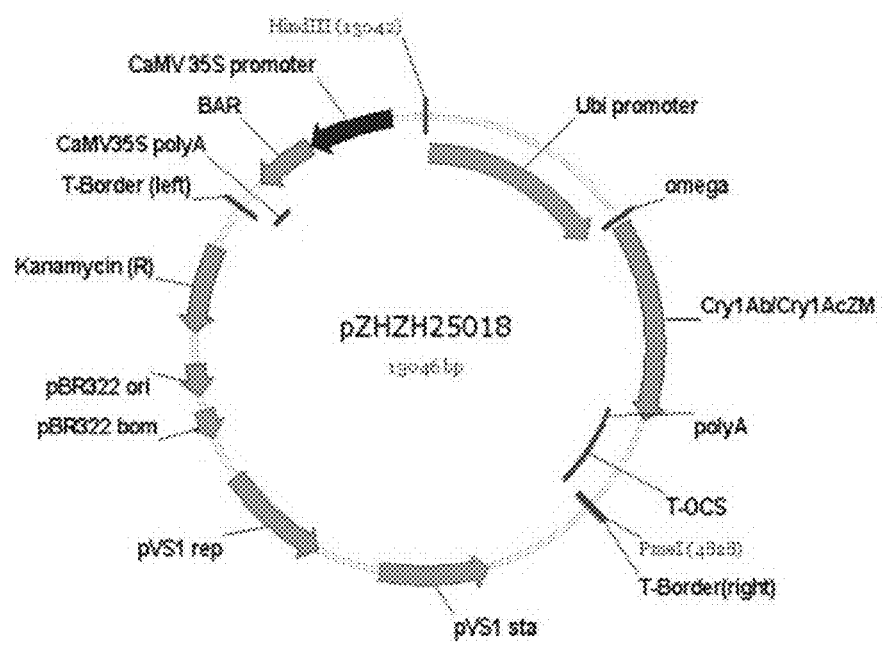

The vector pzz00015 was digested with HindIII+PmeI, and Ubi-Cry1Ab/Cry1AcZM-Tocs was linked to the digestion sites to obtain an expression vector named pZHZH25018 containing two expression components Ubi-Cry1Ab/Cry1AcZM-Tocs and 35s-BAR-T35spolyA, as shown in FIG. 1E.

(III) Construction of pZHZH25020

1. An existing vector containing 35S promoter (with SalI digestion site at the 5' end and with BamHI digestion site at the 3' end) was named pzz01143.

2. pzz01143 was double digested with SalI+BamHI to obtain a 35S promoter fragment, and a sticky end produced therefrom was blunted with T4DNA polymerase.

3. The promoter Rbcs on a fragment Rbcs-Cry1Ab/Cry1AcZM-Tnos contained in an existing vector pzz01191 can be removed by double digestion with HindIII+PstI.

Figure 1F:
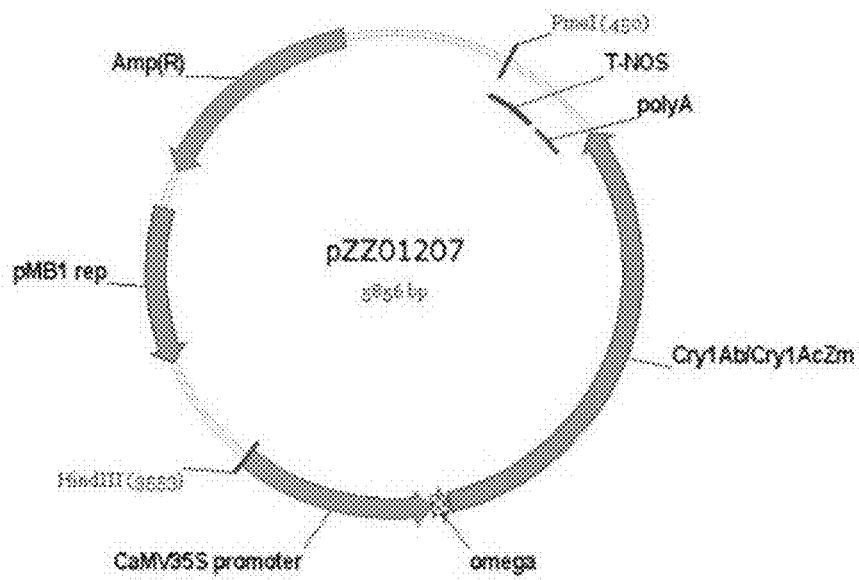
Figure 1G:
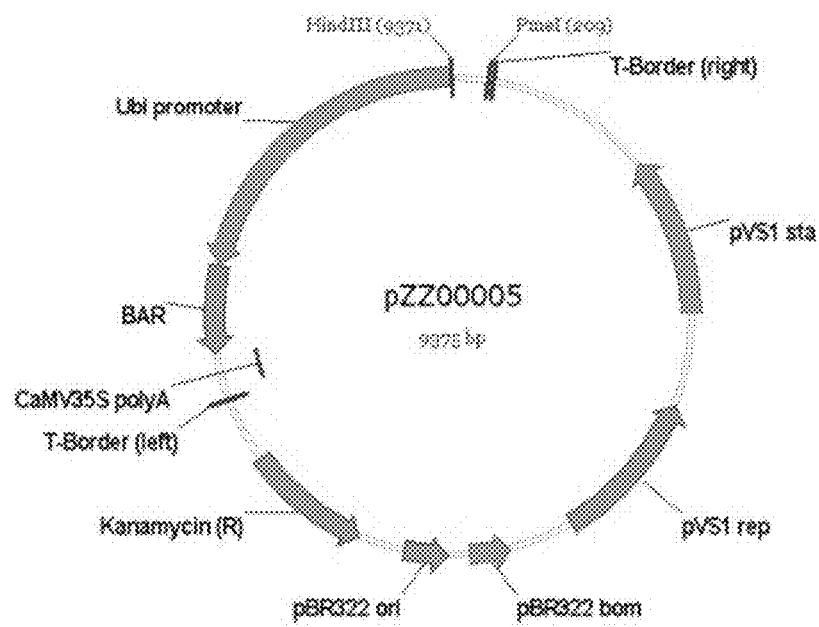

4. pzz01191 was doubly-digested with HindIII+Pst, a Rbcs promoter fragment was removed, and a sticky end of the remaining fragment was blunted with T4DNA polymerase. The 35S promoter fragment obtained in step 2 was linked thereto to obtain a vector named pzz01207 containing 35S-Cry1Ab/Cry1AcZM-Tnos (FIG. 1F).

5. A vector pzz00005 (FIG. 1G) was constructed with pCambia3300 (with an element Ubi-BAR-T35spolyA) as its backbone and digestion sites of HindIII and PmeI into which exogenous fragments can be added.

6. The vector pzz01207 was digested with HindIII+PmeI to obtain a fragment 35S-Cry1Ab/Cry1AcZM-Tnos.

Figure 1H:
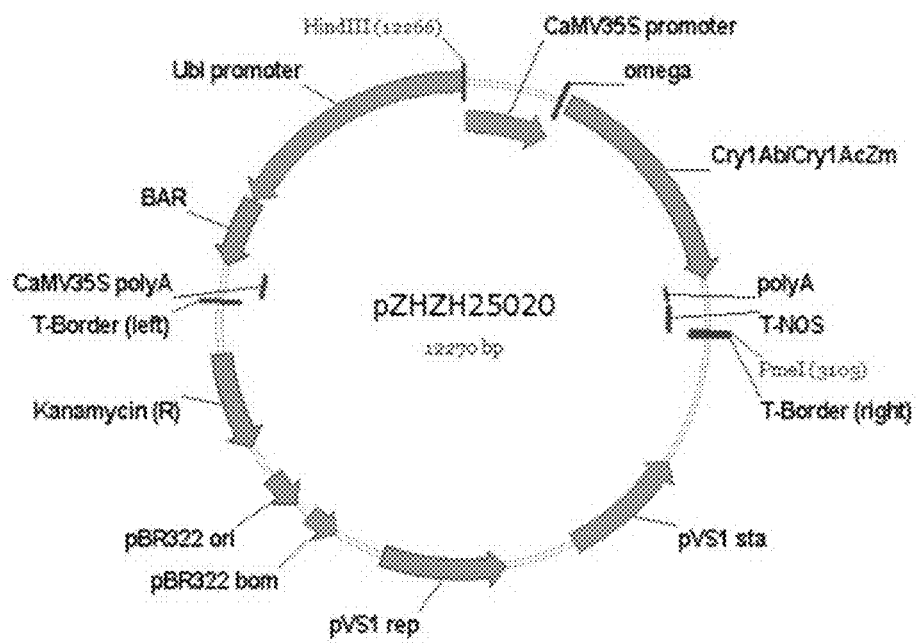

7. The vector pzz00005 was digested with HindIII+PmeI, and 35S-Cry1Ab/Cry1AcZM-Tnos was linked to the digestion sites to obtain an expression vector named pZHZH25020 containing two expression components, i.e., 35S-Cry1Ab/Cry1AcZM-Tnos and Ubi-BAR-T35spolyA, as shown in FIG. 1H.

(IV) Construction of pZHZH25022

1. A cloning vector pzz01194 was used for the construction

2. An existing vector containing a fragment Ubi-Cry1Ab/Cry1AcZM-Tocs (a fragment PolyA on Cry1Ab/Cry1AcZM, together with Tocs, can be obtained by double digestion with EcoRI+PmeI) was named pzz01206.

3. An existing vector containing a fragment 35S-Cry1Ab/Cry1AcZM Zm-Tnos (a fragment PolyA on Cry1Ab/Cry1AcZM, together with Tnos, can be removed by double digestion with EcoRI+PmeI) was named pzz01207.

4. pzz01206 was double-digested with EcoRI+PmeI to obtain a fragment polyA+Tocs.

Figure 1J:
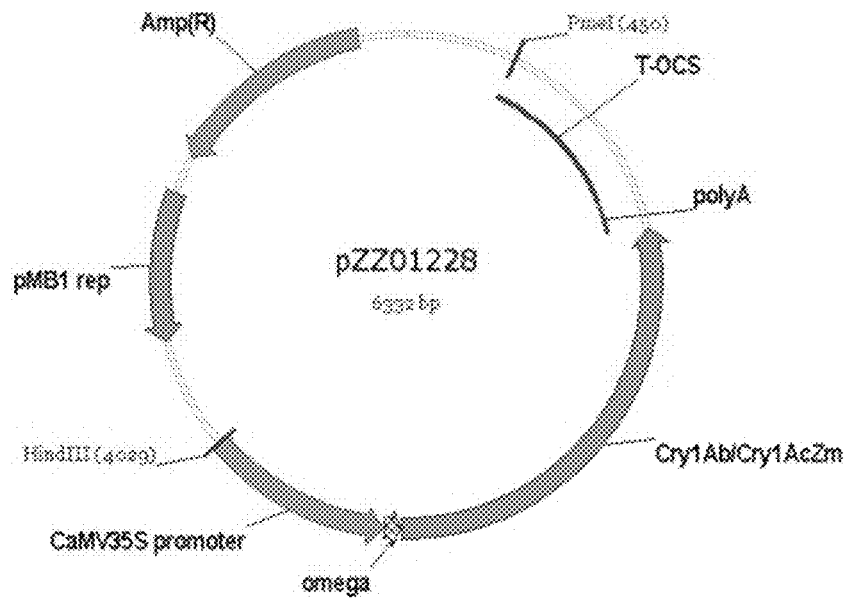

5. pzz01207 was doubly-digested with EcoRI+PmeI to remove a fragment polyA+Tnos. The fragment polyA+Tocs obtained in step 5 was linked thereto to obtain a vector named pzz01228 containing 35S-Cry1Ab/CryAc Zm-Tocs (FIG. 1J).

6. A vector pzz00005 was constructed with pCambia3300 (with an element Ubi-BAR-T35spolyA) as its backbone and digestion sites of HindIII and PmeI into which exogenous fragments can be added.

7. The vector pzz01228 was digested with HindIII+PmeI to obtain a fragment 35S-Cry1Ab/Cry1Ac ZM-Tocs.

Figure 1K:
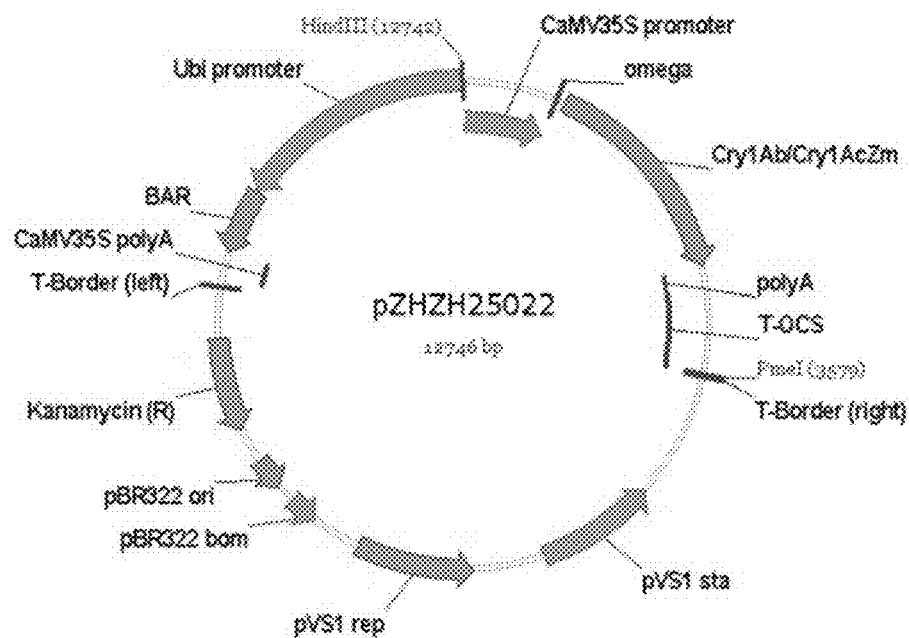

8. The vector pzz00005 was digested with HindIII+PmeI, and 35S-Cry1Ab/Cry1Ac Zm-Tocs was linked to the digestion sites to obtain an expression vector named pZHZH25022 containing two expression elements, i.e., 35S-Cry1Ab/Cry1AcZM Zm-Tocs and Ubi-BAR-T35spolyA, as shown in FIG. 1K.

TABLE 3

Expression Cassette Structure of a Transformation Vector

| No. | Vector No. | Promoter | Structural gene | Terminator | Other genes |
|---|---|---|---|---|---|
| 1 | pZHZH25017 | Ubi | Cry1Ab/Cry1AcZM | Nos | Bar |
| 2 | pZHZH25018 | Ubi | Cry1Ab/Cry1AcZM | Ocs | Bar |
| 3 | pZHZH25020 | CaMV35S | Cry1Ab/Cry1AcZM | Nos | Bar |
| 4 | pZHZH25022 | CaMV35S | Cry1Ab/Cry1AcZM | Ocs | Bar |

Example 3: Genetic Transformation (1) Genetic transformation of maize: vectors DNA pZHZH25017, pZHZH25018, pZHZH25020, pZHZH25022 and other plasmids were transformed into agrobacterium EHA105 by an electroporation method, and were identified prior to use. Maize inbred line Xiang 249 was selfed, and an embryo having a length of 1.5 mm was then used for transformation. Embryos collected from about 200 ears were used as a batch, put in EP tubes to suck out the suspension, co-cultured with an agrobacterium suspension containing 200 μM acetosyringone for 5 minutes, and then transferred to a symbiotic medium and dark-cultured for three days. After dark culture, the embryos were placed on a callus inducing culture medium. After the formation of callus, the embryos were placed on a selective medium containing 5 mg/L bialaphos for selective culture, and were subcultured once every two weeks. After the formation of resistant callus, embryonic callus in good conditions were selected and transferred to a differential medium, and cultured under conditions of 26° C. and 3000 Lux illumination intensity for 16 hours every day. Two weeks later, regrowing seedlings appeared. The regrowing plantlets were transferred to a rooting medium, and were transplanted, after the formation of secondary root, in a small pot with a mixture of nutrient soil and vermiculite (1:3). At the same time, DNA was extracted from leaf samples to identify positive plants by PCR test, and then transplanted into a large flowerpot. After 7 leaves were formed on a plant, bioassay of insect resistance was carried out, and T1 generation seeds were obtained by selfing or hybridization.

(2) Genetic transformation of rice: in this disclosure, the expression of Cry1Ab/Cry1AcZM in rice was tested with japonica rice "Kongyu 131" as the transformation receptor. Insect-resistant and herbicide-resistant genes were introduced into rice by an agrobacterium-mediated genetic transformation method using a vector pZHZH25020, including specific steps of: transforming a constructed expression vector into agrobacterium; infecting embryogenic callus of the rice with an agrobacterium suspension; transferring the callus to a selective medium added with glufosinate to select resistant callus; transferring the resistant callus to a differential medium for differentiation, transferring regrowing seedlings formed by differentiation to a rooting medium, hardening off the seedlings after root formation, and transplanting the seedlings to obtain more than 200 transformants of T0 generation transgenic rice. These transformed plants were analyzed by PCR, the seeds were obtained by selfing of the selected positive plants, and more than 50 transformed T1 plant lines were identified. Analysis on Bt protein expression was performed for T1 generation materials after seeding and sprouting.

Example 4: DNA Molecular Identification of Transgenic Plants Using PCR and Southern Blot (1) PCR Detection Genomic DNA was extracted from T0 generation transgenic maize with a DNA extraction kit of Tiangen Biotech Co., Ltd.

The following reagents were taken out from a refrigerator at −20° C., and then unfrozen: 10×PCR buffer solution (Takara), deoxynucleotide mixture (10 mM, Sigma), forward and reverse primers (forward primer CSP759: 5' CACGCAGATTCCAGCGGTCAA-3' (SEQ ID NO: 4); reverse primer CSP760: 5'-GACGAGGTGAAGGCGTTAGCA-3' (SEQ ID NO: 5)) and DNA template of maize leaves. After being unfrozen, all reagents were shortly centrifuged for a few seconds, and put on ice. A mixed solution of the PCR reaction system was prepared, fully mixed, and shortly centrifuged for a few seconds. PCR reaction system (20 μl): 2 μl of 10×PCR buffer solution (Takara), 0.5 μl of deoxyribonucleotide mixture (10 mM, Sigma), 0.8 μl of a mixture of forward and reverse primers (5 μM), 0.2 μl of r-Taq (5 u, Takara), 1 μl of DNA template of maize leaves, and the rest being dd $H_2O$. The mixed solution was subpacked into 200 μl PCR tubes, to which 1 μL of template DNA was added, and different samples were distinguished by respective markers. The PCR reaction tubes were placed in a Thermo 9700 PCR amplification device, and a preset PCR amplification program was selected to start the reaction. PCR reaction procedure: predegeneration at 94° C. for 2 minutes; and less than 30 cycles as follows: degeneration at 94° C. for 30 seconds, annealing at 58° C. for 30 seconds, extension at 72° C. for 30 seconds; and final extension at 72° C. for 5 minutes.

On completion of the PCR, 5 μl of the PCR product was tested by agarose gel electrophoresis. 1.5% agarose gel was prepared, stained in ethidium bromide (EB) for 10 minutes after electrophoresis at 150V for 25 minutes, and then was photographed in a UV gel imaging system. The gene Cry1Ab/Cry1AcZM was specifically present in the transformation vectors. In this way, a transgenic plant that can amplify the gene specific band is a positive plant, or otherwise, is a negative material. FIG. 2 shows the testing result of transformed maize seedling T0. Lanes 1-6 respectively refer to different T0 generation transgenic plants, as shown in the caption of accompanying drawings. T1 generation plant lines were selfed or hybrid progenies of selected T0 generation plants, and their PCR test result was also positive. The obtained positive plants and plant lines are shown in Table 4.

TABLE 4

Conventional PCR for Identification of Transformed Plants

| No. | Vector No. | Number of positive T0 generation plants | Number of positive T1 generation plant lines |
|---|---|---|---|
| 1 | pZHZH25017 | 120 | 70 |
| 2 | pZHZH25018 | 150 | 80 |
| 3 | pZHZH25020 | 90 | 55 |
| 4 | pZHZH25022 | 95 | 65 |

Note:
The number of positive T1 generation plant lines refers to selfed progenies of T0 generation plant lines.

(2) Southern Blot Identification

Total genomic DNA of the transgenic maize was extracted. The obtained DNA precipitate was dried and then dissolved in deionized water, and its concentration was determined.

A probe was prepared with pZHZH25018 plasmid DNA as the template. A probe of 333 bp for Cry1Ab/Cry1AcZM was synthesized using a PCR DIG Probe Synthesis Kit (article NO. 11636090910) of Roche Company with sequence 4 (SEQ NO 4, CSP759: CACGCAGATTCCAGCGGTCAA and CSP760: GACGAGGTGAAGGCGTTAGCA) as the primer. The amplification system includes: 5 μL (50 pg) of DNA template, 0.5 μL of CSP759 primer, 0.5 μL of CSP760 primer, 5 μL of PCR DIG mixture, 0.75 μL of DNA polymerase, 5 μL of PCR buffer solution (10×) and 33.25 μL of dd$H_2O$. PCR reaction procedure: predegeneration at 94° C. for 5 minutes; and less than 35 cycles as follows: degeneration at 94° C. for 30 seconds, annealing at 55° C. for 30 seconds, extension at 72° C. for 45 seconds; and final extension at 72° C. for 7 minutes. On completion of PCR amplification, the product was kept at 12° C., and the marker effect was detected with 1% gel.

After enzyme digestion of samples, the digested fragments were recovered. A 200 μL digestion system was prepared from 20 μg of maize genomic DNA, 20 μL of restriction enzyme and 20 μL of 10× buffer solution, and was supplemented with dd$H_2O$ to 200 μL. After enzyme digestion for 16 h, 20 μL was tested by electrophoresis to determine whether the digestion effect was complete. The enzyme digestion product was supplemented with ddH$_2$O to 400 μL, to which ¹⁄₁₀ volume of 3 M sodium acetate solution (pH5.2) was added, 4 μl of Dr. GenTLE Precipitation Carrier was added, and 2.5 volume of anhydrous ethanol was added. The mixture was fully mixed, and centrifuged at 12000 RPM at 4° C. for 15 minutes. The precipitate was dissolved in 50 μl of ddH$_2$O, to which 5 μl of 6× loading buffer was added.

After electrophoresis of the DNA on 0.8% gel at 20V for 16 h, excess lanes and loading wells were cut off. The remaining gel was treated with a degeneration solution twice, for 15 minutes each time, and was gently shaken on a shaking bed. Then it was treated with a neutralization buffer twice, for 15 minutes each time, and gently shaken on a shaking bed. It was washed with ultrapure water once, treated with 20×SSC for 10 minutes, followed by trarsmembrane processing with a whatman system for more than 4 hours.

On completion of the trarsmembrane, the membrane was cross-linked by a UV crosslinker on Whatman 3MM filter paper soaked with 10×SSC for 3-5 minutes. The membrane was simply washed with ddH$_2$O, and then dried in air. Both the hybridization and development processes were carried out in accordance with the operation manual of Roche DIG Detection Kit I (article no. 11745832910).

In this experiment, the copy number of exogenous genes integrated into the maize genome and the similarities and differences between the transformed plants were detected. By digesting genomic DNA respectively with restriction enzymes HindIII and NcoI, the result of the copy number integrated into the maize genome was obtained (FIG. 3). FIG. 3 shows the results of molecular hybridization of HindIII-digested maize genomic DNA of a transformed T1 generation plant line to a Cry1Ab/Cry1AcZM-specific probe having a length of 333 bp. Lanes 1 and 6 are for a negative control Xiang 249; Lanes 2 and 7 are for T1-1; Lanes 3 and 8 are for T1-2; Lanes 4 and 9 are for T1-3; and Lanes 5 and 10 are for T1-4 material. M is a lane for molecular weight marker with the number of base pairs. Under the enzyme digestion conditions by either enzyme, a positive band is respectively shown, indicating that a single copy of an exogenous gene was inserted. The two enzymes showed positive bands, indicating that the exogenous gene copy was inserted. With this method, a number of single copy transformed plants with different transformation vectors at different insertion sites were identified. Among 4 vectors (pZHZH25017, pZHZH25018, pZHZH25020 and pZHZH25022), more than 15 single copy transformed plants were identified for each transformation vector.

Example 5: Determination of Bt Protein Expression in Transgenic Plants

The contents of insect-resistant proteins in transgenic plants were determined by immunostrip and enzyme-linked immunosorbent assay (ELISA).

(I) Identification by Immunostrip

Proteins in plant tissues were tested using the AntiCry1Ab (Cry1Ac) test strip available from a biotechnology company in the following steps. Sampling: certain quantity of to-be-tested tissues (leaves, filaments, etc.) were sampled, ground in the presence of a water solution of PBS (1 ml of solution added to 0.2 g of sample), and centrifuged. The supernatant was tested by dipping the testing end of the test strip into the sample. The result was observed 5-10 minutes later. If the control line is darkened, it means that the test is normal, and whether the test line is darkened means whether the solution contains the to-be-tested protein. As shown in the figure, bands can be detected from all transgenic plants with positive PCR test results, while bands were not detected from the wild type control materials, indicating that an exogenous gene Cry1Ab/Cry1Ac can express proteins in transgenic maize cells. FIG. 4 shows the immunoassay result of six T0 generation plants of transformed maize seedlings, where: materials 1-6 were positive, and material 7 was negative. The protein expression in single copy transformed plants of a number of different transformation vectors was identified by this method. Among the four vectors (pZHZH25017, pZHZH25018, pZHZH25020 and pZHZH25022), more than fifteen T0 generation transformed seedlings were identified for each transformation vector.

(II) Detection of Insect-Resistant Protein Contents in Leaves by ELISA.

The content of Bt protein encoded by Cry1Ab/Cry1AcZM in leaves of different transformed maize and rice plants was determined using a double antibody sandwich enzyme-linked immunosorbent assay (ELISA) kit. The enzyme-linked immunosorbent assay kit was a product of Shanghai Youlong Biotech Co., Ltd., and the specific operation process followed the manufacturer's manual. The Bt protein content was determined with a Tecan infinite M200pro Microplate spectrophotometer equipped with software i-control 1.10, and the data were recorded at 450 nm. A standard curve was made based on the standard protein sample concentrations and the recorded OD values, and the Bt protein content in the to-be-tested sample (μg/g fresh weight material) was calculated.

(1) Detection of Bt Protein Content in Maize Leaves

ELISA detection process is described briefly as follows: fresh leaves were sampled from T1 generation (pZHZH25018) maize growing at the phase of 9 leaves and 1 phyllophore. 250 μl of sample extracting solution (PBS) was added to 5 mg fresh weight of samples weighed with an electronic balance (0.0001 g sensitivity). The total protein was extracted from the homogenate of leaves obtained by steel ball method, and was centrifuged at 4000 rpm for 5 minutes. The supernatant was sucked up and diluted for ELISA detection.

A standard curve ($R^2$=0.993) was made based on standard protein Cry1Ab/Cry1Ac provided by the manufacturer to quantitatively measure the to-be-tested samples. The concentration of unknown samples and the Bt protein content in leaves (the number of micrograms per gram fresh weight of leaves) were calculated based on the standard curve equation, where the number of samples from each group was n=12. The results of western blotting are provided in Table 5A.

TABLE 5A

Bt Protein Content in Maize Leaves of Different Transformed Plants

| Material No. | Average value (μg/g) | Standard error | Remark |
|---|---|---|---|
| 1 | 5.772684* | 0.682009 | |
| 2 | 5.435507* | 0.212927 | |
| 3 | 5.427482* | 0.473412 | |
| 4 | 5.427482* | 0.473412 | |
| 5 | 4.08721 | 0.277786 | Positive control |
| 6 | 0.015 | 0.12 | Negative control |

Note:
*means significant difference from positive control.

Test materials No. 1-5 were selected transformed plant samples, material No. 5 was the internal positive control sample, and material No. 6 was the negative control Xiang 249. Statistical analysis has shown that the Bt protein content in materials No. 1-4 was significantly higher than that in material No. 5.

The experiments have proven that the Bt gene tested in the disclosure was well expressed in leaves of the selected transformed maize plants, and the content of the protein Cry1Ab/Cry1Ac in fresh leaves was in the range of 5-6 µg/g.

(2) Detection of Bt Protein Content in Rice Leaves

ELISA detection process is described briefly as follows: fresh leaves were sampled from T1 generation (pZHZH25020) rice growing at the phase of 7 leaves and 1 phyllophore. 250 µl of sample extracting solution (PBS) was added to 5 mg fresh weight of samples weighed with an electronic balance (0.0001 g sensitivity). The total protein was extracted from the homogenate of leaves obtained by steel ball method, and was centrifuged at 4000 rpm for 5 minutes. The supernatant was sucked up and diluted for ELISA detection.

A standard curve ($R^2=0.997$) was made based on standard protein Cry1Ab/Cry1Ac provided by the manufacturer to determine and analyze the to-be-tested samples. The concentration of unknown samples and the Bt protein content in leaves (the number of micrograms per gram fresh weight of leaves) were calculated based on the standard curve equation, where the number of samples from each group was n=6. Leaves of five different transformed plants were determined, and the results are listed in Table 5B.

TABLE 5B

Bt Protein (Cry1Ab/Cry1Ac) Content in Rice Leaves on Different Transformed Plants

| Material No. | Average value (µg/g) | Standard error | Remark |
|---|---|---|---|
| T1-1 | 4.345954 | 0.77963 | |
| T1-2 | 1.216633 | 0.348865 | |
| T1-3 | 4.58597 | 0.77226 | |
| T1-4 | 6.992914* | 0.423833 | |
| T1-5 | 7.902484* | 0.883617 | |
| CK-6 | 5.032986 | 0.495962 | Positive control |
| CK-7 | −0.01 | 0.1 | Negative control |

Note:
*means significant difference from positive control.

Test materials No. T1-1 to T1-5 were selected transformed rice plants, material No. 6 was the internal positive control, and material No. 7 was the negative control. Statistical analysis has shown that the protein contents in materials No. 4-5 were significantly higher than that in the internal positive control material No. 6.

The experiments have proven that the Bt gene tested in the disclosure was well expressed in leaves of the selected transformed rice plants, and the contents of the protein Cry1Ab/Cry1Ac in fresh leaves were in the range 4-8 µg/g.

Example 6: Identification of Herbicide Resistance in T0 and T1 Plants

Identification of herbicide resistance: seeds obtained by selfing or test cross of positive T0 generation plants were sown in a greenhouse, the herbicide resistance of T1 generation plants growing at phase of 6 to 8 leaves was identified, and the plants free of resistant genes were removed. A gene Cry1Ab/Cry1AcZM and a glufosinate-resistant gene were both in the sequence of left and right borders of T-DNA, and were both transformed into recipient maize. In the case of selfing of T0 generation and T1 generation, the proportion of isolated herbicide resistance in T2 generation plant populations was one of the bases for judging genetic homozygosity.

The herbicide sprayed was produced by Bayer CropScience (China) Co., Ltd with a soluble liquid containing an active ingredient of 18% glufosinate ammonium. Determination of tolerance identification concentration of glufosinate ammonium: recommended dosage of the herbicide is 150-300 ml/Mu (diluted with 30-40 kg of water), i.e., diluted 100-267 times. Therefore, in the disclosure, GLA solution diluted by 100 times was applied on the top second leaf (cutting off leaf apex as inspection marker) on the transformed maize plant at whorl stage (6 to 8 fully expanded leaves). 4-5 days later, the herbicide tolerance was observed and recorded. The results have shown that a large number of transformed maize plants with leaves highly resistant to glufosinate ammonium were obtained in this experiment. Among the four vectors (pzhzh225017, pZHZH25018, pZHZH25020 and pZHZH25022), more than 50 T0 generation transformed seedlings and subsequent T1 and T2 plant lines were identified for each transformation vector.

Example 7: Insect Resistance Bioassay of Transgenic Maize Plants

Insect resistance bioassay experiment of T0 and T1 plant materials was carried out by using two methods: detached leaf method and detached filament method.

(1) Determination of In Vitro Resistance of Transgenic Maize to Corn Borers Using Detached Leaf Identification Method When 6-7 leaves were formed on to-be-tested maize, the top second leaf was, after cutting off the leaf apex part, placed in a culture dish having a diameter of 9 cm, and filter paper was wetted with 1300 µL of distilled water at the bottom of the culture dish to keep high humidity. 10 newly hatched larvae of corn borers were inoculated in each culture dish, which was sealed with medical proof fabric having good air permeability. Triplicate samples were collected from each plant, a non-transgenic inbred line Xiang 249 was used as a negative control, and an internal positive control sample was additionally established. The larvae were cultured at a temperature of 28° C. and humidity of 75% under the conditions of illumination: dark=14:10. Four days later, the number of dead insects in each dish was checked to calculate corn borer mortality and corrected mortality. Corrected mortality (%)=(mortality of treated samples−mortality of control samples)/(1−mortality of control samples).

The results have shown that transformed maize plants with leaves highly resistant to corn borers were obtained in this experiment (as shown in FIG. 5A and Table 6).

TABLE 6

Insect Resistance Performance of Leaves on T0 Generation Transformed Plants of Different Bt Gene Sequence Expression Cassettes

| Vector No. | Proportion of corrected mortality = 100% | Proportion of corrected mortality < 100% | Ranking of insect resistance |
|---|---|---|---|
| pZHZH25017 | 50% | 50% | 4 |
| pZHZH25018 | 67% | 33% | 2 |
| pZHZH25020 | 58% | 42% | 3 |
| pZHZH25022 | 75% | 25% | 1 |
| Negative control | 0 | 0 | 5 |

Note:
12 positive plants were tested for each T0 generation vector.

(2) Detached Filament Identification Method

Outstanding T1 generation transformed plants were sown in a greenhouse. Fresh filaments on maize in blossom were taken into the greenhouse, and put in a culture dish after twining several times for each filament. The insect inoculation method and culture conditions were the same as those in the detached leaf method. Four days later, the larvae survival condition of corn borers was checked. The results have shown that transformed maize plants with filaments highly resistant to corn borers were obtained in this experiment (as shown in FIG. 5B and Table 7).

TABLE 7

Insect Resistance Performances in Outstanding T1 Generation Transformed Plants of Different Bt Gene Sequence Expression Cassettes

| Vector No. | Detached leaves of T1 generation (corrected mortality) | Detached filaments of T1 generation (corrected mortality) |
|---|---|---|
| pZHZH25017 | 100% | 100% |
| pZHZH25018 | 100% | 100% |
| pZHZH25020 | 100% | 100% |
| pZHZH25022 | 100% | 100% |
| Negative control | 0 | 0 |

Note:
Three optimal transformed plants were tested for each T1 generation vector, triplicate samples were set for each transformed plant, and the classification was calculated based on the results.

Seeds were harvested by selfing or crossbreeding of transgenic plants with leaves highly resistant to corn borers with the transformed plant line as the unit for further analysis, identification and transgenic breeding of progenies.

Example 8: Comparison with Existing Genes

Based on the nucleotide sequence in the prior art (CN1037913C), transformation and insect resistance identification of transformed seedlings were carried out in the same way as those in Examples 2-6. Based on the description in Example 2, a vector driven by a promoter CaMV35S and having a terminator Nos was constructed with the sequence in CN1037913C, and was named pCN1037913C. pCN1037913C was transferred into Xiang 249 through the agrobacterium-mediated transformation technology. A number of plants with an exogenous insect-resistant Bt gene were obtained by molecular identification, all of which were different transformed plants of pCN1037913C vector. Then, based on Example 5, corn borer resistance in a series of transformed maize plants of pCN1037913C was compared with the corn borer resistance in a plurality of transformed maize plants of different vectors created in the disclosure under identical conditions. The results of insect resistance performance in T0 generation transformed plants of different Bt gene sequence expression cassettes were listed in Table 8. The results of insect resistance performance in outstanding T1 generation transformed plants of different Bt gene sequence expression cassettes were listed in Table 9.

TABLE 8

Insect Resistance Performances in Leaves on T0 Generation Transformed Plants of Different Bt Gene Sequence Expression Cassettes

| Vector No. | Number of plants of corrected mortality = 100% (Proportion) | Number of plants of corrected mortality < 100% (Proportion) | Ranking of insect resistance |
|---|---|---|---|
| pZHZH25017 | 50% | 50% | 4 |
| pZHZH25018 | 67% | 33% | 2 |
| pZHZH25020 | 58% | 42% | 3 |
| pZHZH25022 | 75% | 25% | 1 |
| pCN1037913C | 17% | 83% | 5 |

Note:
Twelve positive plants were tested for each T0 generation vector.

TABLE 9

Insect Resistance Performance in Outstanding Transformed Plants of Different Bt Gene Sequence Expression Cassettes

| Vector No. | Detached leaves of T1 generation (corrected mortality) | Detached filaments of T1 generation (corrected mortality) | Ranking of insect resistance |
|---|---|---|---|
| pZHZH25017 | 100% | 100% | 1 |
| pZHZH25018 | 100% | 100% | 1 |
| pZHZH25020 | 100% | 100% | 1 |
| pZHZH25022 | 100% | 100% | 1 |
| pCN1037913C | 95% | 50% | 5 |

Note:
Three optimal transformed plants were tested for each T1 generation vector, triplicate samples were set for each transformed plant, and the classification was calculated based on the results.

The results have shown that the insecticidal activity of Bt gene sequence Cry1Ab/Cry1AcZM designed in the disclosure is better than that of the existing sequences. The T0 generation leaves, and T1 generation leaves and filaments in the outstanding transgenic plants have stronger ability to kill corn borers.

All references cited herein are incorporated hereby by reference and are used for all purposes to the same extent as if each individual publication was specifically and individually indicated to be incorporated by reference for all purposes. When the publications and patents or patent applications incorporated herein by reference conflict with the disclosed contents contained in the specification, the contents in the specification replacement and/or are superior to any such conflicting reference materials.

All numbers used to show the quantities of components, chromatographic conditions and the like in the DESCRIPTION and CLAIMS should be understood as being modified by the term "about" in all cases. Therefore, unless otherwise specified, numeric parameters stated in the DESCRIPTION and appended CLAIMS are approximations, and may be changed based on the desired performance to be acquired in the disclosure.

The embodiments described herein are provided only by way of examples and are not intended to be restricted in any way. The DESCRIPTION and EXAMPLES are considered as exemplary only, with a true scope of the disclosure being limited by the appended claims. As is apparent to those skilled in the art, many modifications and alterations to the disclosure may be made without departing from the spirit and scope of the disclosure. Therefore, these modifications or improvements made without departing from the spirit of the disclosure are all encompassed within the scope of protection of the disclosure.

What is claimed is:

1. An isolated nucleic acid molecule comprising the nucleotide sequence as set forth in SEQ ID NO: 1.

2. An expression cassette comprising the nucleic acid molecule according to claim 1; and optionally, said nucleic acid molecule being operably linked to a Ubi promoter and an Ocs terminator, or to a Ubi promoter and a Nos terminator, or to a CaMV35S promoter and an Ocs terminator, or to a CaMV35S promoter and a Nos terminator.

3. An expression vector comprising the expression cassette according to claim 2; optionally, said expression vector further comprising an Ωsequence; optionally, said expression vector further comprising a Kozak sequence; optionally, said expression vector further comprising a PolyA sequence; and optionally, said expression vector further comprising a Bar gene.

4. A host cell comprising the expression vector according to claim 2; optionally, said host cell being a plant cell or a prokaryotic cell; and optionally, said host cell being an *Escherichia coli* cell or an Agrobacterium cell.

5. A method for producing a transgenic plant, wherein the transgenic plant is obtained by transforming a plant by using the expression vector according to claim 3; optionally, said plant is a monocotyledonous plant; and optionally, said plant is selected from the group consisting of maize, rice, wheat, oat, barley, highland barley, millet, sorghum and sugarcane.

6. A method for producing a transgenic seed, wherein the transgenic seed is produced from the transgenic plant produced by the method according to claim 5.

7. A method for controlling a population of a lepidopteran pest, the method comprising feeding the population of the lepidopteran pest with a transgenic plant obtained by the method according to claim 5; optionally, said plant being a monocotyledonous plant; optionally, said plant being selected from the group consisting of maize, rice, wheat, oat, barley, millet, sorghum and sugarcane; and optionally, said lepidopteran pest being *Ostrinia furnacalis* or *Ostrinia nubilalis*.

8. A method for killing a lepidopteran pest, the method comprising feeding the lepidopteran pest with an insecticidally effective amount of a transgenic plant obtained by the method according to claim 5; optionally, said plant being a monocotyledonous plant; optionally, said plant being selected from the group consisting of maize, rice, wheat, oat, barley, millet, sorghum and sugarcane; and optionally, said lepidopteran pest being *Ostrinia furnacalis* or *Ostrinia nubilalis*.

9. A method for reducing the damage of a lepidopteran pest to a plant, the method comprising stably integrating an expression vector into the genome of the plant, wherein said expression vector comprises a nucleic acid molecule encoding a lepidopteran pest-resistant gene, and said nucleic acid molecule comprises the nucleotide sequence as set forth in SEQ ID NO: 1; optionally, said plant is a monocotyledonous plant; optionally, said plant is selected from the group consisting of maize, rice, wheat, oat, barley, millet, sorghum and sugarcane; and optionally, said lepidopteran pest is *Ostrinia furnacalis* or *Ostrinia nubilalis*.

10. A transgenic plant comprising an expression cassette integrated into a genome thereof, wherein said expression cassette comprises a nucleic acid molecule encoding a lepidopteran pest-resistant gene, said nucleic acid molecule comprises the nucleotide sequence as set forth in SEQ ID NO: 1; optionally, said plant is a monocotyledonous plant; and optionally, said plant is selected from the group consisting of maize, rice, wheat, oat, barley, millet, sorghum and sugarcane.

11. An isolated nucleic acid molecule comprising the complement of the nucleic acid molecule according to claim 1.

* * * * *